(12) United States Patent
Anderson

(10) Patent No.: US 8,939,015 B2
(45) Date of Patent: Jan. 27, 2015

(54) TESTING IMBIBITION OF FLUID

(75) Inventor: Valerie Anderson, Hardwick (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 343 days.

(21) Appl. No.: 13/544,835

(22) Filed: Jul. 9, 2012

(65) Prior Publication Data
US 2013/0014561 A1 Jan. 17, 2013

(30) Foreign Application Priority Data

Jul. 12, 2011 (GB) .................................. 1111936.9

(51) Int. Cl.
*G01N 15/08* (2006.01)
*G01N 33/24* (2006.01)

(52) U.S. Cl.
CPC ...................................... *G01N 33/24* (2013.01)
USPC ............................................................ 73/38

(58) Field of Classification Search
CPC ............................... G01N 15/08; G01N 33/24
USPC ............................................................ 73/38
See application file for complete search history.

(56) References Cited

U.S. PATENT DOCUMENTS

| | | | | |
|---|---|---|---|---|
| 4,552,011 | A | * | 11/1985 | Wiley .............................. 73/1.69 |
| 5,263,360 | A | * | 11/1993 | Blauch et al. ...................... 73/38 |
| 5,679,885 | A | * | 10/1997 | Lenormand et al. ............... 73/38 |
| 5,698,772 | A | * | 12/1997 | Deruyter et al. ................... 73/38 |
| 5,858,791 | A | | 1/1999 | Lemaire |
| 7,464,582 | B2 | * | 12/2008 | Egermann et al. ................. 73/38 |
| 8,024,960 | B2 | * | 9/2011 | Fleury et al. ....................... 73/38 |
| 2012/0241149 | A1 | * | 9/2012 | Chen et al. ............... 166/250.01 |

OTHER PUBLICATIONS

Combined Search and Examination Report of British Patent Application Serial No. 1111936.9 dated Oct. 18, 2011: pp. 1-5.
Al-Attar, "Experimental study of spontaneous capillary imbibition in selected carbonate core samples," Journal of Petroleum Science and Engineering, 2010, vol. 70: pp. 320-326.
Bachmann et al., "Extended methodology for determining wetting properties of porous media," Water Resources Research, 2003, vol. 39(12): pp. SBH11-1-SBH11-14.
Dang-Vu et al., "Wettability determination of solids isolated from oil sands," Colloids and Surfaces A: Physicochem. Eng. Aspects, 2009, vol. 337: pp. 80-90.
Hammond et al., "Spontaneous and Forced Imbibition of Aqueous Wettability Altering Surfactant Solution into an Initially Oil-Wet Capillary," Langmuir, 2009, vol. 25(21): pp. 12591-12603.
Hammond et al., "Forced and Spontaneous Imbibition of Surfactant Solution into an Oil-Wet Capillary: The Effects of Surfactant Diffusion Ahead of the Advancing Meniscus," Langmuir, 2010, vol. 26(9): pp. 6206-6221.

(Continued)

*Primary Examiner* — Daniel S Larkin

(57) ABSTRACT

A convenient method of testing imbibition of one or more imbibant fluids by a matrix of particles with a fluid already therein, comprises making a body 4 of packed particles with a matrix fluid filling the interstices between the particles, placing an imbibant fluid in each of a plurality of capillaries 6, 7, partially inserting each capillary into the body 4 so that part of the capillary with imbibant fluid therein projects from the body 4 and observing time for fluid to be taken from each capillary into the body. The method allows comparison of multiple imbibant fluids by placing each fluid in a respective capillary.

6 Claims, 2 Drawing Sheets

(56) References Cited

OTHER PUBLICATIONS

Hammond et al., "Spontaneous Imbibition of Surfactant Solution into an Oil-Wet Capillary: Wettability Restoration by Surfactant-Contaminant Complexation," Langmuir, 2011, vol. 27: pp. 4412-4429.

Hapgood et al., "Drop Penetration into Porous Powder Beds," Journal of Colloid and Interface Science, 2002, vol. 253: pp. 353-366.

Karimaie et al., "Experimental investigation of oil recovery during water imbibition," Journal of Petroleum Science and Engineering, 2006, vol. 52: pp. 297-304.

Wu et al., "An Experimental Study of Wetting Behavior and Surfactant EOR in Carbonates With Model Compounds," SPE Journal, 2008, vol. 13(1): pp. 26-34.

* cited by examiner

TESTING IMBIBITION OF FLUID

CROSS-REFERENCE TO RELATED APPLICATION

This application claims priority to British Patent Application Serial No. GB1111936.9 filed Jul. 12, 2011, which is incorporated herein by reference in its entirety.

FIELD AND BACKGROUND OF THE INVENTION

This invention relates to testing the imbibition of fluid by a porous material which already contains another fluid. Although the invention is not necessarily limited to a specific application, it is useful for testing the imbibition of fluid by the rock of an oil reservoir. Such testing may be required when it is intended to recover oil by injecting another fluid.

Injecting a fluid to displace oil and drive it out of a reservoir may be done in the context of producing heavy oil from an underground reservoir or in the context of enhanced oil recovery after initial production has partially depleted the reservoir. It is desirable and indeed may be it essential that it is energetically favorable for the injected fluid to enter the rock pores.

For instance, oil reservoirs which are naturally fractured carbonate rock often comprise high-permeability fractures in low-permeability matrix rock. A water-flooding process may be used to drive oil from the reservoir. In such a process, water is pumped into the reservoir to displace the oil, forcing it away from the injection well towards adjacent wells from which it is produced. If the matrix is water-wet (i.e., it is energetically favorable for water to enter the matrix) then water-flooding can be an effective means of recovering more oil. However, if the matrix is oil-wet (i.e., it is energetically unfavorable for water to enter the matrix) water-flooding is not effective because the water flows in the fractures and cannot be forced through the porous rock matrix.

In such cases oil can be produced by pumping a fluid (the imbibant) which is spontaneously imbibed by the rock matrix (the imbibor). An aqueous imbibant fluid may be a surfactant solution but other fluids such as brines may also be considered. Spontaneous imbibition of an aqueous solution into an oil-bearing rock matrix depends upon parameters such as the wettability of the rock, the interactions between the fluid and the rock, and the interactions between the fluid and the in-situ oil. These interactions can be difficult to quantify.

When it is intended to use an injected fluid to displace oil, it is desirable to test imbibition and optimize the fluid for the reservoir rock and the existing reservoir fluids. If the imbibant is a surfactant solution and the imbibor is an oil-bearing reservoir rock (which also is likely to contain a formation brine), the surfactant may be absorbed into the oil or the formation brine, onto the oil-imbibant interface, or onto the imbibor pore surface.

Tests to look at isolated interactions (e.g., measurements of surface tension, or measurements of surfactant adsorption onto a mineral surface) may be carried out and the results used to predict the combined effect of the interactions. However, it is also useful to make a direct experimental test of imbibition of fluid by the porous reservoir matrix. This is customarily done by the Amott cell test which is carried out by immersing a sample of the porous medium in the fluid and measuring the amount of fluid that it imbibes or the amount of oil that is produced from the sample. However, a rock core (or slice of a rock) is needed for each test which may last several days (not including preparation time). These tests can be time consuming and may need a lot of material.

There have been proposals for experimental methods in which a droplet of water is placed on a porous material which is dry, so that its pore space is filled only with air, and the time for the droplet to penetrate into the porous material is measured. This has been proposed as a measurement of the wettability of the porous material which is just one of the parameters mentioned above which affect imbibition.

The present inventor points out that the result in such a test is affected by the area of contact between water droplet and the porous material and cannot provide a true measurement of imbibition.

SUMMARY OF THE INVENTION

This invention provides a method of testing imbibition of an imbibant fluid by a matrix of particles with a fluid therein, comprising making a body of packed particles with a matrix fluid filling the interstices between the particles, placing an imbibant fluid in a capillary, partially inserting the capillary into the body, so that part of the capillary with imbibant fluid therein projects from the body and observing time for fluid to be taken from the capillary into the body. Use of a capillary facilitates observation of imbibition: what is directly observed is the position of the liquid surface in capillary. In embodiments, the observation made may be the time for the surface of the liquid in a capillary to move between two marked points on the capillary. In some embodiments, the internal diameter of a capillary lies in a range from 0.5 mm to 2 mm.

A body of packed rock particles with matrix fluid in the interstices provides a model of underground porous rock. The matrix fluid may be hydrophobic, for example a hydrocarbon oil, or it may be hydrophilic, for example a saline solution or it may contain both hydrophilic and hydrophobic liquids. In some embodiments the matrix fluid is a hydrocarbon oil phase comprising at least 90 wt % hydrocarbon oil and the imbibant fluid is an aqueous solution.

An advantage of this test method is that it can be carried out more rapidly than an Amott cell test. Also, less material is required. The contact area between the imbibant fluid and the body of packed particles is dependent on capillary size and not on the size of a droplet. Thus use of a capillary avoids the problem that droplet size is a variable that cannot be fully controlled. Moreover, it is possible to run multiple tests concurrently by inserting a number of capillaries into the body of particles at different positions. If multiple capillaries are used, some or all of them may contain different imbibant fluids. Provided they are spaced apart from one another, the imbibition of fluid from each one will not interfere with the others. In this way the rate of imbibition of several different imbibant fluids can be compared directly. These fluids might for instance differ in one or more of surfactant type, surfactant concentration, salt type and salt concentration. It is of course possible that a plurality of capillaries could contain the same fluid, in order to obtain more than one measurement, and further capillaries could contain one or more different imbibant fluids.

Embodiments of the method of this invention may be carried out with the aim of comparing a number or fluids with each other. The aim of testing a number of imbibant fluids might be to select the combination of surfactant type and concentration, together with salt type and concentration which will optimize the oil recovery rate. The faster the imbibition of the imbibant, the faster must be the recovery of oil.

A body of packed particles may be made with samples of rock, oil and aqueous phase from an underground reservoir and then used to test candidate fluids contemplated for injection to displace oil from the reservoir.

The imbibition of a fluid will occur if it is favorable for pore surfaces to be wetted by the fluid. In order to observe this it is generally desirable to have substantial surface area available and hence it is desirable that particles have a small size which enhances their surface to volume ratio. It may be desirable to employ a mean particles size smaller than 100 micron for instance a mean size in a range from 1 or 5 micron up to 50 or 100 micron.

The rock particles may be material found in particulate form, e.g., sand grains, or may be made by comminuting larger pieces of rock. For example calcium carbonate particles could be used to make a body simulating a carbonate rock. Another possibility is that part of a rock core taken as a sample below ground could be ground to powder form. Yet another possibility is to take rock cuttings collected from drilling mud as a well is being drilled and use these to make a body of packed particles after cleaning them from drilling mud and if necessary grinding them to smaller size.

One possibility for providing the body of packed particles is that it is initially made with a salt solution followed by drawing oil into the body of packed particles and allowing the body and fluid to equilibrate. This would allow the properties of the rock surface, the oil and the salt solution to determine whether the rock remains water-wetted (such that a film of aqueous solution remains between the rock surface and the oil) or becomes oil-wetted.

When making the body of packed particles some mechanical pressure may be applied in order to push particles together, although the amount of applied pressure need not be large. A mixture of particles and liquid may be formed into a packed body on a filter.

DETAILED DESCRIPTION

Figures 1, 2:
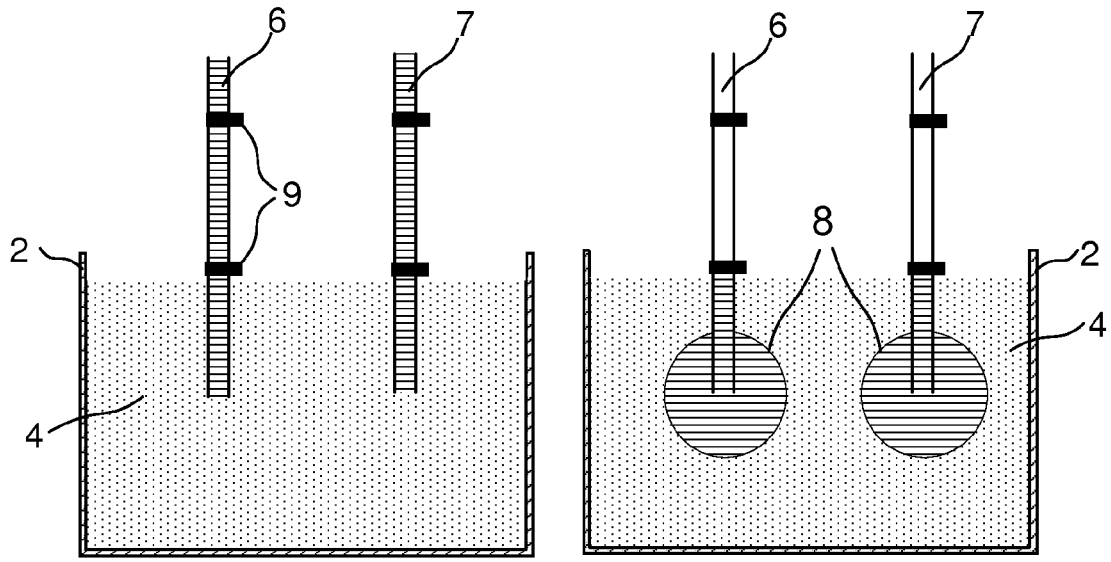
FIGS. 1 and 2 schematically illustrate a test in accordance with this invention.

FIG. 1 schematically illustrates testing in accordance with this invention. A container 2 holds a cake 4 composed of rock particles with fluid in the interstices between the particles. A capillary 6 is filled with an imbibant fluid to test and then partially inserted into the cake 4 as shown in FIG. 1. A second capillary 7 is filled with a second imbibant fluid and this is likewise partially inserted.

Over time the fluids in the capillaries are imbibed but the capillaries were placed far enough apart that the volumes of imbibed fluid, depicted as circles 8 in FIG. 2, remain separate and so the imbibition of one fluid does not affect imbibition of the other.

To perform the test, each capillary has two markers 9 attached to it. The lower marker also indicates how far to insert the capillary into the cake 4. The time for the fluid meniscus in the capillary to drop from the upper marker to the lower one is timed with a stopwatch.

Figure 3:
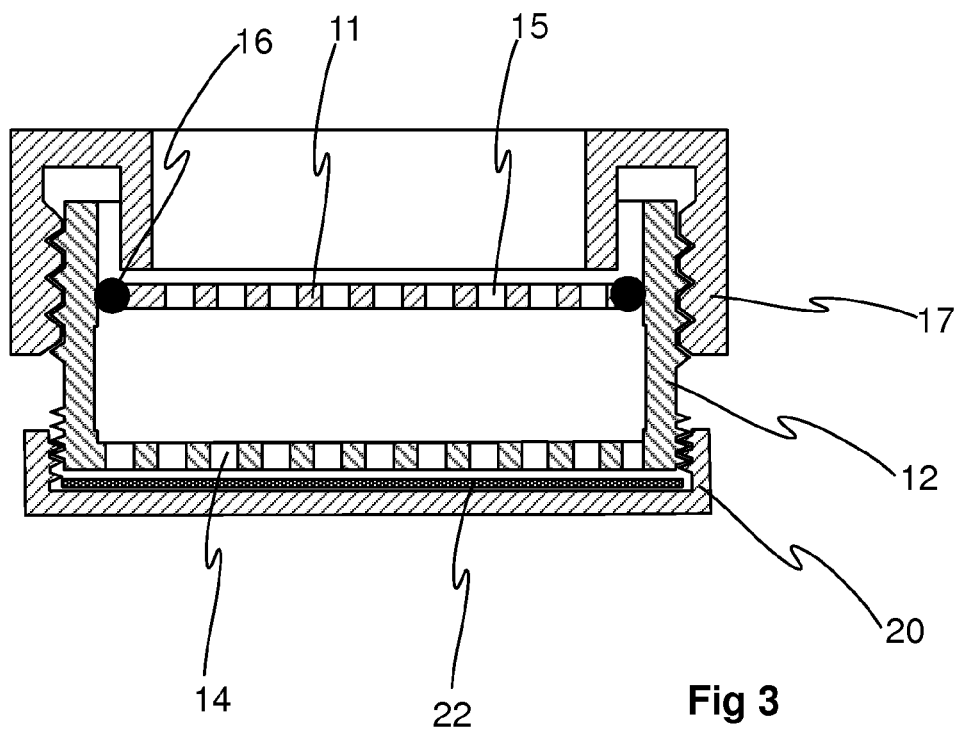
FIG. 3 is a cross-sectional view of an apparatus used in making a cake of particles.

Apparatus used to make a cake of packed particles is shown in FIG. 3. A cylindrical body 12 with a flat base has an array of holes 14 through its base. An upper plate 11 with a similar array of holes 15 fits within the body 12. The plate 11 is encircled by an O-ring 16 so that the plate 11 is a friction-fit within the cylindrical body 12.

An annular cap 17 engages a screw thread on the upper part of body 12 so that turning the cap can press the plate 11 down and so compress material between the plate 11 and the base of the body 12. When required, a bottom cover piece 20 can be screwed onto the body 12, closing the holes 14 with a rubber sheet 22 and preventing drainage.

Figure 4:
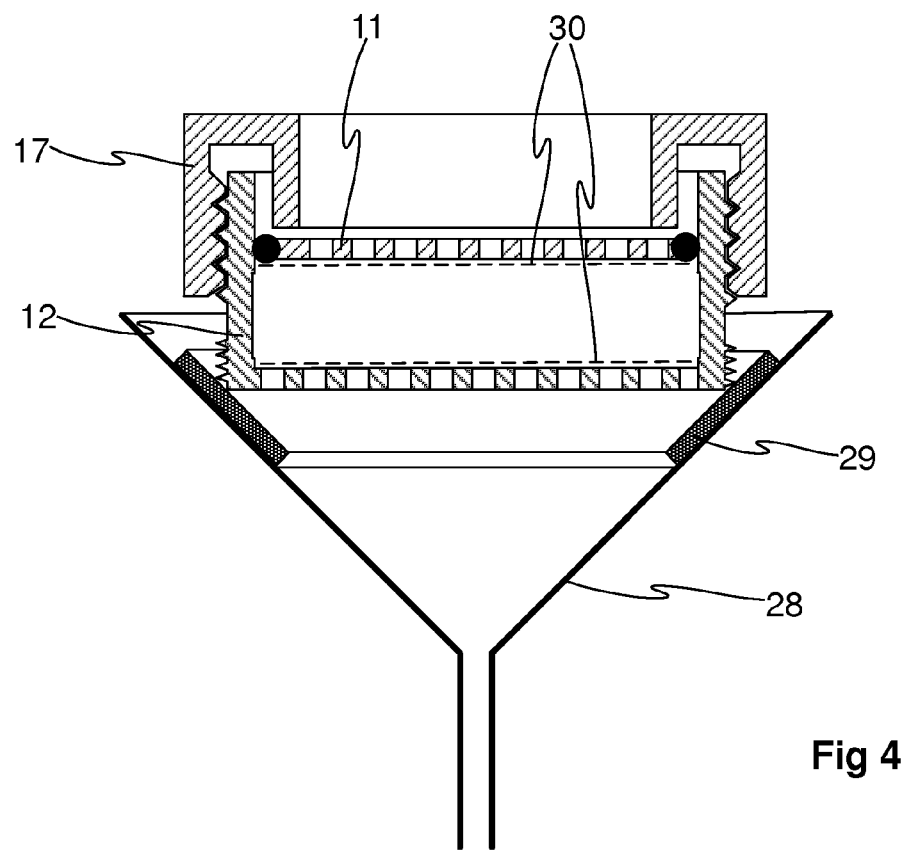
FIG. 4 is a cross-sectional view showing the apparatus in use to form a cake.

As shown by FIG. 4, to make a cake of rock particles, the body 12 without the bottom cover 20 is placed on a funnel 28 with a rubber cone 29 in the funnel to provide a seal between the body 12 and the funnel.

The procedure used here to make the cake is as follows: two pieces of pre-wetted filter paper 30 are placed on the lower plate. A slurry of brine and calcium carbonate powder is poured in and allowed to settle. Once most of the brine has drained leaving a firm but still wet cake, two more pieces of filter paper 30 are placed on top of the cake and the upper plate 11 is put on. The cap 17 is slowly screwed on forcing the upper plate 11 down and compressing the cake. Care is taken that this is done slowly enough that the filter paper 30 does not burst, but quickly enough that the cake does not drain of brine completely (such that a small layer of brine is visible on the top plate; this is to minimize air in the sample).

Once a cake of particles is in place, the brine can be displaced with oil by pouring oil on to the top of the plate 11 within the body 12 and applying vacuum to the funnel 28 to suck the oil into the cake. After the oil has been drawn into the cake, the body 12 can be taken off the funnel and fitted with the bottom cover piece 20 to prevent further drainage. The cake may be left to age before imbibition tests are carried out.

The above description of apparatus and procedure for making a cake of particles is given as an example. Within the scope of this invention, it would be possible to form the cake in other ways, for example to form it by centrifuging rather than filtration. Packing the particles into a cake could also be done solely by filtration without mechanical pressure.

EXAMPLE

Two cakes were made using calcium carbonate particles of mean particle size (diameter of equivalent sphere) of approximately 10 microns slurried in 2 wt % sodium chloride solution.

Apparatus as shown in FIGS. 3 and 4 was used to make each cake. The body 12 had an internal diameter of approximately 6 cm and the compressed cake had a thickness of approximately 3 cm. After the cake had been formed in the body 12 of the apparatus, a mixture of 98.5 wt % decane and 1.5 wt % naphthenic acids was poured onto the top plate 11 and drawn into the cake by vacuum applied to the funnel 19 beneath. The body 12 was then taken off the funnel and the bottom cover 20 was fitted.

Both cakes were used to test imbibition of surfactant solutions containing from 0 to 10 wt % of dodecyltrimethlyammonium bromide (DTAB) in aqueous 2 wt % potassium chloride solution.

Glass capillary tubes having a length of 127 mm and an internal diameter of 1.3 mm were filled with sample surfactant solutions. This was easily done by partial immersion in a beaker of the solution. The capillary was then inserted into the cake to a depth of 1.5 cm and the fall of the meniscus from an upper mark on the capillary to a lower marker 3 cm below the upper marker was timed. It was found possible to insert seven capillaries into each cake.

Figure 5:
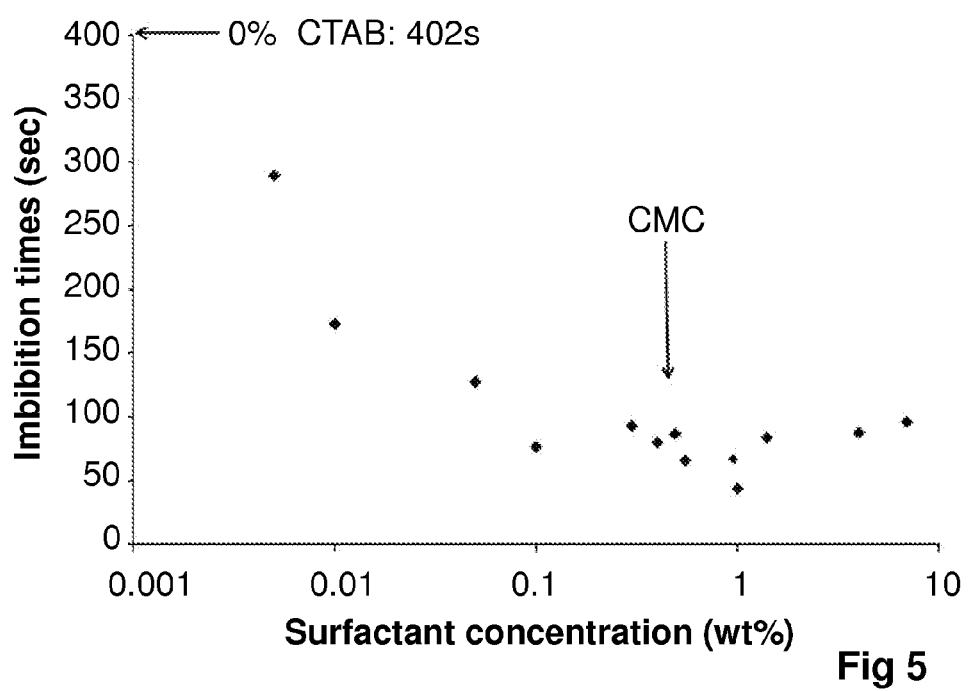
FIG. 5 shows the results obtained in an example.

Fourteen surfactant concentrations were tested in this way. The concentrations tested with one cake were picked at random. The remainder was tested with the second cake. The results obtained are shown in FIG. 5. It can be seen that the data points would (approximately) lie on a curve with imbibition times decreasing as the surfactant concentration is increased until the critical micelle concentration of the surfactant (at about 0.8 wt % surfactant) is reached.

The invention claimed is:

1. A method of testing imbibition of an imbibant fluid by a matrix of particles with a fluid therein, comprising:
    making a body of packed particles with a matrix fluid filling the interstices between the particles;
    placing an imbibant fluid in a capillary;
    partially inserting the capillary into the body, so that part of the capillary with imbibant fluid therein projects from the body; and
    observing time for fluid to be taken from the capillary into the body.

2. A method according to claim 1, wherein the time which is observed is the time for the surface of the imbibant fluid in the capillary to travel between two points on the capillary.

3. A method according to claim 1, wherein the body of particles is formed by filtration of a slurry of the particles.

4. A method according to claim 1, wherein the body of particles is formed by filtration of a slurry of the particles followed by introduction of the matrix fluid.

5. A method according to claim 1, comprising:
    placing an imbibant fluid in each of a plurality of capillaries;
    partially inserting each capillary into the body, so that part of the capillary with imbibant fluid therein projects from the body; and
    observing time for fluid to be taken from each capillary into the body.

6. A method according to claim 1 or any other previous claim wherein the matrix fluid is a hydrocarbon oil phase and the or each imbibant fluid is an aqueous solution.

\* \* \* \* \*